(12) United States Patent
Daalmans et al.

(10) Patent No.: US 6,686,735 B2
(45) Date of Patent: Feb. 3, 2004

(54) METHOD AND DEVICE FOR THE IN SITU DETECTION OF THE DEGREE OF CONVERSION OF A NON-MAGNETIC PHASE IN A FERROMAGNETIC PHASE OF A METALLIC WORK PIECE

(75) Inventors: Gabriel Daalmans, Hoechstadt (DE); Ruediger Doell, Nuremberg (DE); Klaus Weinzierl, Nürnberg (DE)

(73) Assignee: Siemens Aktiengesellschaft (DE)

( * ) Notice: Subject to any disclaimer, the term of this patent is extended or adjusted under 35 U.S.C. 154(b) by 0 days.

(21) Appl. No.: 10/168,958
(22) PCT Filed: Dec. 12, 2000
(86) PCT No.: PCT/DE00/04429
§ 371 (c)(1),
(2), (4) Date: Sep. 23, 2002
(87) PCT Pub. No.: WO01/46682
PCT Pub. Date: Jun. 28, 2001

(65) Prior Publication Data
US 2003/0038630 A1 Feb. 27, 2003

(30) Foreign Application Priority Data
Dec. 22, 1999 (DE) ......... 199 62 184
(51) Int. Cl.⁷ ......... G01N 27/72; G01R 33/12
(52) U.S. Cl. ......... 324/243; 324/225; 324/227
(58) Field of Search ......... 324/225, 227, 324/228, 233, 234, 239–243, 203, 236

(56) References Cited

U.S. PATENT DOCUMENTS

| | | | |
|---|---|---|---|
| 3,449,661 A | 6/1969 | Puidak | 324/237 |
| 4,686,471 A | 8/1987 | Morita et al. | 324/243 |
| 4,740,747 A | 4/1988 | Kawashima et al. | 324/239 |
| 5,270,646 A | * 12/1993 | Kihlberg et al. | 324/207.16 |

FOREIGN PATENT DOCUMENTS

| | | |
|---|---|---|
| DE | E19523519 | 6/1995 |
| EP | 0177626 | 10/1984 |
| EP | 0884588 | 3/1997 |
| WO | WO9315396 | 8/1993 |

* cited by examiner

Primary Examiner—Jay Patidar
(74) Attorney, Agent, or Firm—Baker Botts LLP

(57) ABSTRACT

A method and measuring device for the in situ detection of the γ-α phase transformation of strip steel. The detection takes place on the basis of the eddy currents of the non-magnetic phase, which are caused from the workpiece when an electromagnetic excitation field is applied, and on the basis of response fields which are generated by the magnetic phase which may be present. At least one electromagnetic excitation field which acts on the workpiece is generated by means of at least one excitation coil, and a response field which results from the application of the excitation field is measured by means of at least one detector measurement coil. The resulting measurement signal, which is dependent on the distance between the measuring device and the workpiece, is used to detect the degree of transformation.

24 Claims, 1 Drawing Sheet

METHOD AND DEVICE FOR THE IN SITU DETECTION OF THE DEGREE OF CONVERSION OF A NON-MAGNETIC PHASE IN A FERROMAGNETIC PHASE OF A METALLIC WORK PIECE

CROSS-REFERENCE TO RELATED APPLICATIONS

This is a national application for International Application No. PCT/DE00/04429 which was filed on Dec. 12, 2000 and which published in German on Jun. 28, 2001, which in turn claims priority from 199 62 184.5, which was filed on Dec. 22, 1999 of which the following is a

FIELD OF THE INVENTION

The invention relates to a method and measuring device for the in situ detection of the degree of transformation of a nonmagnetic phase into a ferromagnetic phase of a metallic workpiece after a thermomechanical treatment. More specifically, the invention relates to the detection of the degree of γ-α phase transformation of a steel workpiece in strip form using a measuring device which is arranged in close proximity to the workpiece. The detection takes place on the basis of the eddy currents of the nonmagnetic phase, which are caused when an electromagnetic excitation field is applied to the workpiece, and on the basis of response fields which are generated by the magnetic phase which may be present. At least one electromagnetic excitation field which acts on the workpiece is generated by means of at least one excitation coil, and a response field which results from the application of the excitation field is measured by means of at least one detector measurement coil. The resulting measurement signal, which is dependent on the distance between the measuring device and the workpiece, is used to detect the degree of transformation.

BACKGROUND OF THE INVENTION

The mechanical properties of high-quality steel sheet which is produced during a hot-rolling process is dependent not only on the composition of the steel, but also on the way in which the hot steel sheet is cooled when it leaves the rolling train. Cooling initiates a recrystallization process which is dependent on the prevailing temperature and the holding time, with the nucleus density of a phase which forms being particularly time-dependent. When the steel sheet is being cooled, in addition to a nonmagnetic phase, known as the γ-phase, a ferromagnetic phase, known as the α-phase, is also formed. Depending on the cooling rate during cooling, the phases are frozen without the phases being in an equilibrium state, i.e. the proportions of phases can be varied as a function of the cooling rate, i.e. the cooling ramp which is passed through. In this context the steel composition also plays a role, since the temperatures at which a new phase is formed are dependent on the steel compositions. The phase transitions which result for a defined steel composition are to be found in the iron-carbon phase diagram.

The possibility of varying the phase proportions by means of a defined cooling process, however, presupposes that the temperature of the metal can be determined as accurately as possible, so that it can be detected when the formation of a certain phase commences. Although it is possible to determine the temperature, for example on the basis of measurement of the heat radiated by the metal, or by means of infrared scanning, the measured values which these measurement processes supply are highly inaccurate, since the oxide layer which forms on the metal strip surface distorts the measurement results. Accordingly, it would be desirable to measure the temperature of the metal below the oxide layer, but this is not possible with the above mentioned processes.

The phase transition from the nonmagnetic γ-phase to the ferromagnetic α-phase, which takes place as a function of the specific steel composition at a precisely determined temperature (which can be worked out on the basis of the iron-carbon phase diagram,) can be effected by means of an eddy-current measuring method. As part of this method, an electromagnetic excitation field is generated and acts on the metallic workpiece. The nonmagnetic phase and the ferromagnetic phase react differently to this field. In the nonmagnetic phase, the electrons of the metallic workpiece move as a function of the electromagnetic field which is present and screen the field. The movement of electrons leads to eddy currents, which in turn generate an opposite field which attenuates the outer excitation field which is applied. The response of the nonmagnetic phase therefore leads to attenuation of the electromagnetic field which is present.

The magnetic phase, by contrast, reacts in the opposite way. The coupling of the magnetic moments means that they are oriented in the direction of the excitation or primary field which is present. The magnetic field resulting from the orientation amplifies the excitation field. Overall, therefore, two opposite processes occur when the nonmagnetic and ferromagnetic phases are present.

If a suitable detector coil which is arranged close to the metallic workpiece is now used to measure the response of the metallic workpiece, at a workpiece temperature which lies above the temperature of phase transition to the α-phase, a low resulting overall field is measured, which results from the attenuation of the primary field by the eddy current response. As soon as the nucleation of the α-phase commences, the resulting field which can be measured by means of the detector coil changes on account of the field fraction of the magnetic phase, which boosts the primary field. This jump can be measured very accurately, and consequently a precise temperature can be determined therefrom. On account of the increasing proportion of magnetic phase during the cooling operation, the resulting field also changes to an increasing extent, so that the temperature-dependent degree of transformation can be determined on the basis of the measured value obtained.

In practice, however, it is not possible to determine the degree of transformation by means of the eddy-current measuring method described above. This results from the movement of the steel sheet during the measurement. The hot steel sheet which comes out of the rolling mill is moved continuously past the stationary measuring device toward a cooling section. However, the movement is not uniform since the steel sheet wobbles and clatters over the conveying rollers. This non-uniform movement results in a number of problems. The strength of the magnetic field which is generated by the eddy currents is dependent on the distance from the workpiece surface to the detector coil, and decreases very considerably as the distance increases. On account of the wobbling of the sheet with respect to the stationary detector coils, the recorded measurement signal changes as a function of the movement of the steel sheet, since the eddy-current field changes continuously as the strip vibrates. Furthermore, the electromagnetic excitation field not only penetrates into the workpiece but also is reflected thereby. The wobbling alone results in an interfering signal which affects the measurement signal.

A further problem is the high metal temperature itself. The temperature of the relevant phase transition is approximately 900° C. The high temperature leads to a certain temperature-dependent change in the shape of the measurement configurations and the detector coils. If a plurality of coils are distributed over the length of the cooling section, it is scarcely possible to obtain results which are suitable for comparison, since the change in shape results in a change in the distance between the individual distributed coils and the metal strip. Changes in shape may even cause difficulties in relation to the individual coil, since the temperature of the metal sheet in the region of the detector coils may change as a function of the cooling operation which is being carried out at that particular time.

U.S. Pat. No. 4,686,471 discloses a measuring system for recording the degree of transformation, which operates in accordance with the method described in the introduction, with one excitation coil and two detector coils being provided in this system. The excitation coil and the detector coils all lie in one plane, and the detector coils are at different distances from the excitation coil.

SUMMARY OF THE INVENTION

The present invention therefore provides a method which enables the in situ detection of the degree of transformation which is extremely precise, and which comprises the steps of measuring a response field, which results from the application of the excitation field, by means of two distance-measuring coils, which are at different distances from the workpiece, for receiving two measurement signals, the level of which is dependent on the distance, and which are used to determine a distance-dependent calculation value. Thereafter, the detection of the degree of transformation is made on the basis of the measurement signal and the calculation value.

DETAILED DESCRIPTION OF THE INVENTION

According to the method of the present invention, the actual distance of the measuring device from the workpiece is measured. For this purpose, it is particularly preferred that two distance-measuring coils are used at different distances from the workpiece, i.e. the steel strip. The fact that the magnetic field of the eddy currents is highly dependent on the distance between the workpiece surface and the measuring device means that two different signals are obtained. From these signals, it is possible to determine a calculation value which is dependent on the distance and provides a measure of the actual distance. For this purpose it is possible, for example, to detect the ratio of the coil voltages, which is independent of the level of the eddy currents, i.e. the material property, but is dependent on the distance. In this case, therefore, the measurement signal used is the coil voltage.

Therefore, on account of the distance-dependent calculation value which is determined, there is a continuous measure of the actual distance. The measurement signal which is obtained in the detector measurement coil, for example the induced voltage which can be tapped off at that coil, is for its part dependent on the excitation current, i.e. the excitation field, and a function which is dependent on the distance of the measuring device and on the degree of transformation. Therefore, in general terms, the following relationship applies:

$V_{detector\ coil} = I_{excitation} \cdot F(h, f\alpha)$, where:

$V_{detector\ measurement\ coil}$=Induced voltage at the detector measurement coil $I_{excitation}$=Excitation current h=Distance between workpiece and measuring device, $f\alpha$=Ferromagnetic phase fraction in the metal sheet.

If the distance between workpiece and measuring device is known, it is possible to detect the ferromagnetic phase fraction and also to determine the metal temperature on account of the fact that the phase fraction can be recorded.

According to the present invention, the excitation coil, in order to generate a first excitation field which generates a first response field which is to be measured by the distance-measuring coils, can be operated with an excitation frequency which is so high that the response field of the nonmagnetic phase is greater than that of the ferromagnetic phase which may be present. According to this embodiment of the invention, therefore, the excitation frequency is selected to be so high that the eddy-current response of the nonmagnetic part is considerably greater than that of the ferromagnetic fraction. Ensuring this is advantageous, since the signal of the magnetic fraction decreases with distance according to a different law from the signal of the nonmagnetic fraction. The ferromagnetic phase fractions can no longer completely follow the high frequencies, or cannot follow them at all. The distance-measuring coils then measure only the response field of the eddy currents. An excitation frequency of $\geq 1$ MHz, in particular $\geq 10$ MHz, is preferably selected.

According to a further preferred embodiment of the present invention, it is possible for the excitation coil, in order to generate a second excitation field which generates a second response field which is to be measured by the detector measurement coil, to be operated with an excitation frequency which is so low that the response field of the nonmagnetic phase is lower than that of the ferromagnetic phase which may be present. The excitation frequency is therefore selected to be so low that the metallic eddy-current response, which is proportional to the third power of the excitation frequency, is insignificant compared to the magnetic response (which is proportional to the product of permeability and excitation frequency). The excitation coil should in this case be acted on by an excitation frequency which is in the kHz range. It is preferable to provide filters for the respective coils, so that each coil measures only the frequency which is of relevance to it.

In addition to the degree of phase transformation, the coercive field strength of the ferromagnetic phase also forms a material parameter which is of interest. To enable this parameter to be detected in parallel with the degree of transformation according to the present invention, it is possible for a low-frequency magnetic field, the field strength of which is greater than the coercive field strength of the workpiece, to be generated by means of the, or a further excitation coil. The response field which is generated by the low-frequency magnetic field is measured by means of the detector measurement coil, and the coercive field strength of the workpiece is determined on the basis of the measurement signal obtained. The field strength of this third excitation field should be controllable and greater than the coercive field of the workpiece. The eddy-current response is measured as a function of this field, and from this it is possible to determine the coercive field strength. The coercive field strength is in this case used as an additional measurement variable for detecting the magnetic phase transition. A filter is expediently connected upstream of the detector measurement coil, and is able to measure the precise measurement of the different response frequencies, i.e. first the response field resulting from the application of the second excitation field, and second the response field resulting from the application of the third excitation field.

Although separate excitation coils can be used to generate the excitation fields, it is preferable to use only one excitation coil, which is acted on by different excitation frequencies. The number of excitation coils used ultimately depends on the specific excitation frequencies. The larger a coil, the more slowly it reacts. Large coils are only used to generate low-frequency fields, i.e. for example the third, low-frequency excitation field. To generate the first two excitation fields, which have a higher frequency, one large coil may be too slow, and consequently in this case it is preferable to use one (or two) smaller, faster coil(s) to generate these two fields.

In addition to the method according to the present invention, the invention also relates to a measuring device for a measuring arrangement for in situ detection of the degree of transformation of a nonmagnetic phase into a ferromagnetic phase of a metallic workpiece after a heat treatment; and more specifically, the degree of $\gamma$-$\alpha$ phase transformation of a steel workpiece in strip form. The measuring device comprises at least one excitation coil for generating an electromagnetic excitation field which acts on the workpiece, and at least one detector measurement coil for measuring a response field which results from the application of the excitation field to the workpiece. The measuring device according to the present invention has two distance-measuring coils which are spaced apart from one another and can be positioned at different distances with respect to the workpiece for separately measuring a response field which results from the application of an electromagnetic excitation field generated by the excitation coil(s) to the workpiece. The distance-measuring coils supply measurement signals which are dependent on distance and can be processed further.

The two distance-measuring coils are preferably aligned one behind the other. They may be arranged in the interior of the annular excitation coil. In the case of distance-measuring coils which are aligned one behind the other, these coils should preferably be arranged in the center of the annular excitation coil, so that the overall result is a symmetrical measurement configuration.

According to a preferred embodiment of the present invention, two detector measurement coils are provided. The second coil is provided to improve the signal-to-noise ratio, for which purpose the measurement signals from the two coils can be cross-correlated and therefore, both coils should be of the same design. Said coil or coils may also be arranged in the interior of the annular excitation coils.

In a further preferred embodiment of the invention, a second excitation coil is provided. One excitation coil is used to generate a first excitation field; and the other excitation coil is used to generate a second excitation field having a frequency which is different from that of the first excitation coil. The first excitation field which is generated provides a first response field which is generated at the workpiece and is measured, for example, by the distance coils. The second excitation field, the frequency of which differs from that of the first excitation field, produces a second response field, which has a different frequency from the first response field, and this frequency can be measured by the detector measurement coil. Corresponding filters allow the frequency of the coils to be measured accurately.

It is further preferred to provide a third excitation coil, which is used to generate a third, low-frequency excitation field.

The annular excitation coil, or coils, the annular detector measurement coils, or coils and one of the annular distance-measuring coils are preferably arranged so as to lie in a single plane.

The present invention further relates to a measuring arrangement for carrying out the method described above. This arrangement comprises a measuring device of the type described above, and at least one excitation unit for exciting the excitation coil(s), at least one receiver unit for receiving the measurement signals from the detector coil(s), at least one receiver unit for receiving the measurement signals from the distance-measuring coils, and at least one processing unit for processing the measurement signals from the distance-measuring coils in order to determine the distance-dependent calculation value, and to determine the degree of transformation on the basis of the calculation value and the measurement signals from the detector measurement coil(s). In this case, the excitation unit for exciting the excitation coil may be designed with different excitation frequencies.

According to the present invention, the processing unit may be designed to determine the calculation value in the form of the ratio of the two measurement signals, which are preferably the induced voltages in the distance-measuring coils.

In a further embodiment of the present invention, the processing unit includes a storage medium in which a multiplicity of different retrievable calculation values are stored, each calculation value being assigned to a different pair of measurement signals. This enables calibration to be effected without having to redetermine it each time, but rather when the measurement signals are input, the calculation value which is assigned to the pair of signals and is stored in the memory is recorded and read out for further processing. The calibration can be carried out by positioning the measuring device next to a metal component having the same conductivity as the steel sheet which is to be produced, at different distances therefrom. Then, for each distance the two distance measurement signals are recorded, and the calculation value is determined and stored as a function of the signals.

It is also possible for the processing device to be designed to determine the coercive field strength of the workpiece on the basis of the measurement signal(s) supplied by the detector measurement coils.

BRIEF DESCRIPTION OF THE DRAWING

Further advantages, features and details of the invention are described herein with reference to exemplary embodiments and drawings, in which.

DETAILED DESCRIPTION OF THE INVENTION

Figure 1:
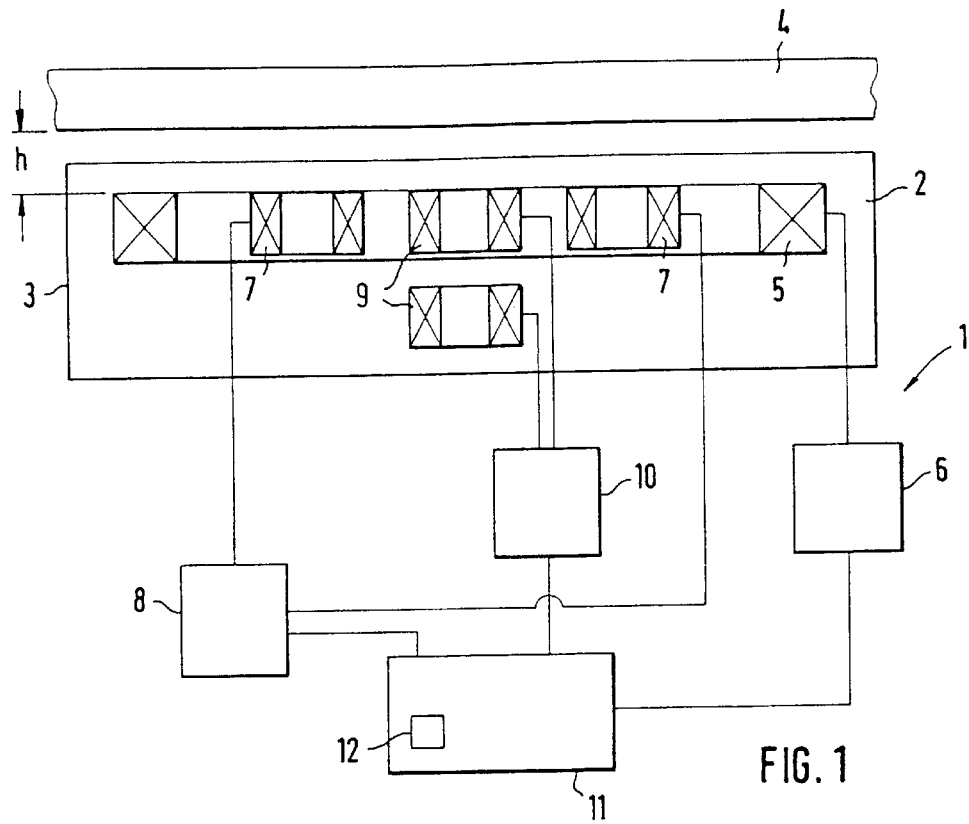
FIG. 1 illustrates an outline sketch of a measuring arrangement according to the invention, having a measuring device according to the invention in a first embodiment.

FIG. 1 shows a measuring arrangement 1 according to the invention which comprises a measuring device 2 according to a first embodiment. An excitation coil 5, which is a relatively large annular coil, is provided in the housing 3 of the measuring device 2, which is arranged close to a metallic workpiece 4 in strip form which is to be examined. The excitation coil 5 is coupled to an excitation unit 6 which is used to excite the excitation coil 5. At least one electromagnetic excitation field of a predetermined frequency is generated by means of the excitation coil 5, and this field acts on the workpiece 4. Depending on the temperature of the workpiece, the workpiece 4 consists of a nonmagnetic, metallic phase, known as the γ-phase, and, if the temperature is sufficiently low and the phase formation commences or has commenced, a ferromagnetic α-phase. The two phases behave differently in response to the effect of the excitation field. In the nonmagnetic γ-phase, electrons are displaced, eddy currents are generated and these currents in turn generate an electromagnetic eddy-current magnetic field which is directed oppositely to the outer excitation or primary field, and as a result, attenuates the latter. In the α-phase, the magnetic moments are oriented in the direction of the excitation field, which boosts the latter. The resulting response field differs depending on whether there is only nonmagnetic phase or whether there is also a fraction of ferromagnetic phase.

This resulting response field is measured by means of two detector measurement coils 7. The detector measurement coils 7 supply measurement signals which are passed to a receiver unit 8 for receiving the measurement signals. An amplifier unit is preferably integrated in this receiver unit in order to amplify the measurement signals, which are preferably the induced coil voltages which have been tapped off. The two measurement signals may be cross-correlated in order to improve the signal-to-noise ratio.

Although the measuring device 2 or the coils are arranged at a defined distance h from the surface of the workpiece 4, this distance changes continuously during the measurement on account of the irregular movement of the workpiece 4 on the conveyor. Since the workpiece tends to wobble with respect to the stationary measuring device 2, the distance h changes continuously. Since the magnetic field of the eddy currents is dependent on the distance from the workpiece surface to the measuring device, and drops considerably as the distance increases, it is necessary to determine the distance continuously in order to be able to reliably detect the degree of transformation. For this purpose, two distance coils 9 are provided in the measuring device 2, and are aligned one behind the other at different distances from the workpiece 4. The distance-measuring coils 9 preferably measure the eddy-current response of the nonmagnetic phase fraction, for which purpose the excitation frequency of the excitation coil 5 is selected to be correspondingly high. The result, therefore, is that two different, distance-dependent measurement signals are obtained. These measurement signals are passed to a receiver unit 10, in which they are preferably amplified by means of an amplifier device (not shown). All the measurement signals, and also the respective excitation frequency, are passed to a processing device 11, in which the degree of transformation from the γ-phase to the α-phase is determined on the basis of the received signals and frequency information.

The processing device 11 has a storage medium 12, in which various distance measurement signal pairs are stored, having been determined as part of a calibration, with a defined calculation value being stored for each pair of distance measurement signals. The actual determination of the degree of transformation takes place on the basis of the signal-dependent, distance-dependent calculation value, which can be read out from the storage medium on the basis of the received distance measurement signals, and on the basis of the signals from the detector measurement coils. The result of detection can be output from the processing device 11 to any desired output medium.

The excitation unit 6 is designed to simultaneously excite excitation coil 5 with different excitation frequencies. On the one hand, excitation coil 5 is operated with a high excitation frequency, so that a first, high-frequency excitation field is generated, the frequency of which is so high that the eddy-current response of the nonmagnetic phase part is considerably greater than that of the ferromagnetic phase fraction. The resulting response field is measured by the two distance-measuring coils 9. Corresponding filters are provided to ensure that the distance-measuring coils 9 record only this frequency range.

Where excitation coil 5 is operated with a lower frequency, in order to generate a second excitation field, the frequency of which is in turn selected to be so low for the eddy-current response of the metallic phase to be low or negligible compared to the response of the ferromagnetic phase. The resulting low-frequency response field is measured by means of the two detector coils. In this case too, corresponding filters are provided. Finally, excitation coil 5 can be excited with a third, low frequency, in order to generate a third, low-frequency magnetic field. The field strength of this magnetic field should be controllable and should be greater than the coercive field of the metal. The low-frequency eddy-current response to this low-frequency excitation field is likewise measured by means of the detector coil 7. The processing device 11 is able to determine the coercive field strength of the metal from these low-frequency measurement signals.

Figure 2:
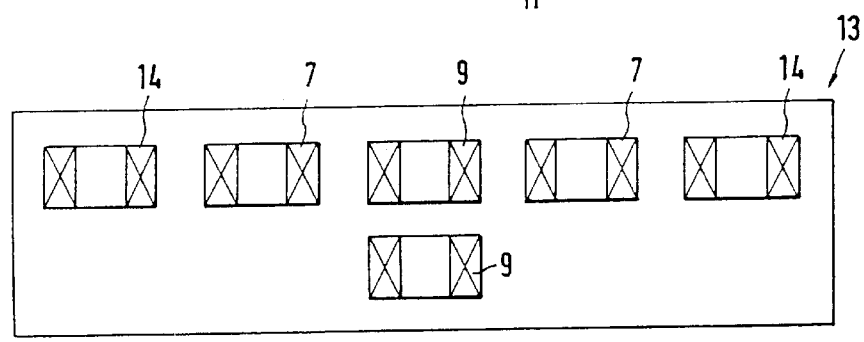
FIG. 2 illustrates a measuring device according to the invention in a second embodiment.

FIG. 2 shows a further embodiment of a measuring device 13 according to the present invention. Like the measuring device 2, device 13 has two distance-measuring coils 9 and two detector measurement coils 7. However, there are two separate excitation coils 14, one of which is used to generate the first two excitation fields described above, while the other excitation coil is used to generate the very low-frequency third field which is used to determine the coercive field strength. This low-frequency field is used, as it were, to run down the hysteresis curve in the region of the coercive field strength. This configuration is advantageous in that the excitation coil which is required to generate this very low-frequency field is relatively slow and unresponsive, and is unable to generate the considerably higher frequencies which are required for generation of the two above mentioned higher-frequency fields.

Figure 3:
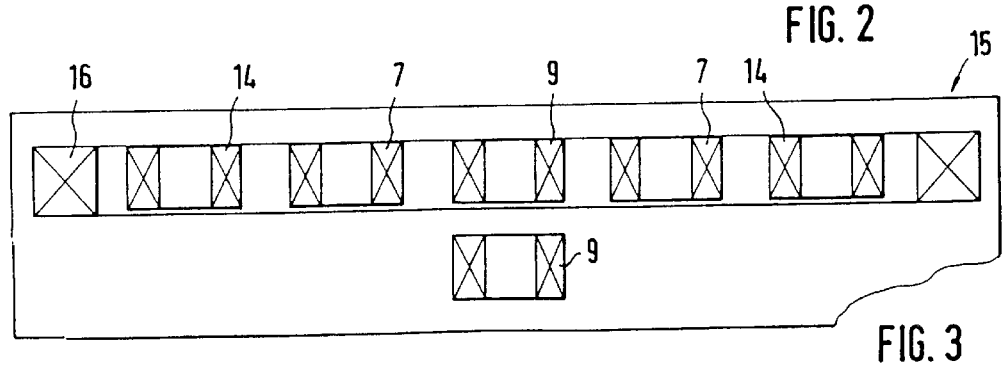
FIG. 3 illustrates a measuring device according to the invention in a third embodiment.

FIG. 3 shows another embodiment of measuring device 15 according to the invention. Once again, the two distance-measuring coils 9 and the two detector measurement coils 7 are provided. Two excitation coils 14 are also provided, one of which is used to generate the first, high-frequency excitation field, while the other is used to generate the second, lower-frequency excitation field. Here, however, there is a third excitation coil 16, which is used to generate the low-frequency excitation field which is used to determine the coercive field strength.

As can be seen from the Figures, all the coils, with the exception of one distance-measuring coil 9, are arranged in a single plane, so that they are therefore all at the same distance from the workpiece surface.

What is claimed is:

1. A method for detection in situ of transformation of a nonmagnetic phase into a ferromagnetic phase of a metallic workpiece after a thermomechanical treatment and degree of said transformation, comprising positioning a measuring device in close proximity to the workpiece, wherein the detection occurs as the result (a) of eddy currents of the nonmagnetic phase, caused by an electromagnetic excitation field applied to the workpiece, and (b) response fields generated by the ferromagnetic phase, at least one electromagnetic excitation field being generated by means of at least one excitation coil, and the resulting response field being measured by means of at least one detector measurement coil, the measurement signal from which, being dependent on the distance from the measuring device to the workpiece, and said signal being used to detect the degree of transformation, further comprising, measuring a response field which results from the application of the excitation field by means of two distance-measuring coils, which are located at different distances from the workpiece, for receiving two measurement signals, said signals having a level which is dependent on the said distances, and which are used to determine a distance-dependent calculation value, and detecting of the degree of transformation on the basis of the measurement signal and the calculation value.

2. The method according to claim 1, wherein a ratio which results from the two measurement signals is used as the calculation value.

3. The method according to claim 1, wherein the excitation coil for generating a first excitation field which generates a first response field to be measured by the distance-measuring coils, is operated with a high excitation frequency so that the response field of the nonmagnetic phase is greater than that of the ferromagnetic phase which may be present.

4. The method according to claim 3, wherein the excitation frequency is ≧1 MHz.

5. The method according to claim 4, wherein the excitation frequency is ≧10 MHz.

6. The method according to claim 1, wherein the excitation coil for generating a second excitation field, which generates a second response field to be measured by the detector measurement coil, is operated with low excitation frequency so that the response field of the nonmagnetic phase is lower than that of the ferromagnetic phase which may be present.

7. The method according to claim 6, characterized in that the excitation coil is acted on by an excitation frequency which is in the kHz range.

8. The method according to claim 1, wherein in a low-frequency magnetic field having a field strength greater than the workpiece's coercive field strength is generated by means of at least one excitation coil, further wherein, the response field which is generated by the low-frequency magnetic field is measured by means of the detector measurement coil, and the coercive field strength of the workpiece is determined on the basis of the measurement signal.

9. The method according to claim 1, further comprising using an additional excitation coil which is acted on by different excitation frequencies.

10. The method according to claim 1, wherein the phase transformation is γ-α phase.

11. A device for measuring an in situ detection of transformation of a nonmagnetic phase into a ferromagnetic phase of a metallic workpiece after a thermomechanical heat treatment and degree of said transformation, comprising at least one excitation coil for generating an electromagnetic excitation field which acts on the workpiece, a detector measurement coil for measuring a response field which results from the application of the excitation field to the workpiece, and two distance-measuring coils, which are spaced apart from one another and positioned at different distances with respect to the workpiece, said distance measuring coils being provided for separately measuring a response-field which results from an electromagnetic excitation field generated by the excitation coil, said distance-measuring coils supplying measurement signals which are distance dependent and can be further processed.

12. The measuring device according to claim 11, wherein the two distance-measuring coils are arranged one behind the other.

13. The measuring device according to claims 11 or 12, wherein the two distance-measuring coils are arranged in the excitation coil's interior.

14. The measuring device according to claims 11 or 12, wherein the two distance-measuring coils, are arranged in the excitation coil's center.

15. The measuring device according to claim 11, further comprising two detector measurement coils.

16. The measuring device according to claims 11 or 15, wherein the detector measurement coil or coils are arranged in the excitation coil's interior.

17. The measuring device according to claim 11, further comprising a second excitation measurement coil, one of said excitation measurement coils being used to generate a first excitation field, and the other excitation measurement coil being used to generate a second excitation field which has a frequency which differs from that of the first excitation measurement coil.

18. The measuring device according to claim 17, further comprising a third excitation coil, which is used to generate a third, low-frequency excitation field.

19. The measuring device according to claim 11, wherein the excitation coil, the detector measurement coil, and the distance-measuring coils are annular and lie in one plane.

20. A measuring arrangement for carrying out the method according to claim 1, comprising a measuring device for measuring an in situ detection of transformation of a nonmagnetic phase into a ferromagnetic phase of a metallic workpiece after a thermomechanical heat treatment and degree of said transformation, comprising at least one excitation coil for generating an electromagnetic excitation field which acts on the workpiece, a detector measurement coil for measuring a response field which results from application of the excitation field to the workpiece, and two distance-measuring coils, which are spaced apart from one another and positioned at different distances with respect to the workpiece, said distance measuring coils being provided for separately measuring a response field which results from an electromagnetic excitation field generated by the excitation coil, said distance-measuring coils supplying supplement signals which are distance dependent and can be further processed and an excitation unit for exciting the excitation coil, a first receiver unit for receiving measurement signals from the detector coil, a second receiver unit for receiving the measurement signals from the distance-measuring coils, and at least one processing unit for processing the measurement signals from the distance-measuring coils in order to determine a distance-dependent calculation value, and to determine a degree of transformation on the basis of the calculation value and the measurement signal from the detector coil.

21. The measuring arrangement according to claim 20, wherein the excitation unit is designed with different excitation frequencies.

22. The measuring arrangement according to claim 20, wherein the processing unit is designed to determine the calculation value in the form of a ratio of two measurement signals.

23. The measuring arrangement according to claim 20, wherein a multiplicity of different retrievable calculation values are stored in a storage medium of the processing unit, each calculation value being assigned to a different pair of measurement signals.

24. The measuring arrangement according to claim 20, wherein the processing device is designed to determine a the coercive field strength of the workpieoe on the basis of the measurement signal(s) supplied by the detector measurement coils.

* * * * *